(12) United States Patent
Carrel et al.

(10) Patent No.: US 9,925,342 B2
(45) Date of Patent: Mar. 27, 2018

(54) AUTOMATIC INJECTION DEVICE

(71) Applicant: Becton Dickinson France, Le Pont de Claix (FR)

(72) Inventors: Franck Carrel, Saint Jean de Vaulx (FR); Lionel Maritan, Pierre-Chatel (FR)

(73) Assignee: Becton Dickinson France, Le Pont de Claix (FR)

( * ) Notice: Subject to any disclaimer, the term of this patent is extended or adjusted under 35 U.S.C. 154(b) by 0 days.

(21) Appl. No.: 14/893,397

(22) PCT Filed: May 22, 2014

(86) PCT No.: PCT/IB2014/000845
§ 371 (c)(1),
(2) Date: Nov. 23, 2015

(87) PCT Pub. No.: WO2014/188263
PCT Pub. Date: Nov. 27, 2014

(65) Prior Publication Data
US 2016/0129202 A1    May 12, 2016

(30) Foreign Application Priority Data

May 24, 2013 (EP) .................................... 13305679

(51) Int. Cl.
*A61M 5/32* (2006.01)
*A61M 5/20* (2006.01)
*A61M 5/315* (2006.01)

(52) U.S. Cl.
CPC ........ *A61M 5/3287* (2013.01); *A61M 5/2033* (2013.01); *A61M 5/31515* (2013.01);
(Continued)

(58) Field of Classification Search
CPC .... A61M 2005/3264; A61M 2005/202; A61M 2005/3261; A61M 5/20333; A61M 2005/2073
See application file for complete search history.

(56) References Cited

U.S. PATENT DOCUMENTS

2003/0105430 A1* 6/2003 Lavi .................... A61M 5/2033
604/136
2006/0224124 A1 10/2006 Scherer
(Continued)

FOREIGN PATENT DOCUMENTS

JP  2007504866 A  3/2007
JP  2009514572 A  4/2009
(Continued)

*Primary Examiner* — Nathan R Price
*Assistant Examiner* — John Doubrava
(74) *Attorney, Agent, or Firm* — The Webb Law Firm

(57) ABSTRACT

The present invention relates to an automatic injection device (1) comprising: a container aligned on a longitudinal axis A and movable between a first position and a second position, in which the needle is inserted, biasing means, laterally spaced with respect to said longitudinal axis A, and coupled to the container for moving it to its second position, via linking means, retaining means (70) for maintaining said biasing means in a first stressed state, deactivating means (80) capable of moving along a transversal direction for releasing said retaining means, triggering means (90) for releasing said deactivating means.

9 Claims, 5 Drawing Sheets

Figure 1E:
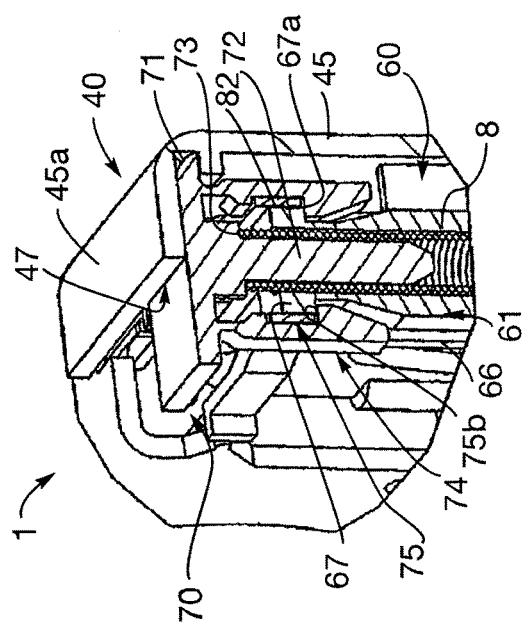

(52) U.S. Cl.
CPC .......... *A61M 5/3202* (2013.01); *A61M 5/326* (2013.01); *A61M 2005/206* (2013.01); *A61M 2005/208* (2013.01); *A61M 2207/00* (2013.01)

(56) References Cited

U.S. PATENT DOCUMENTS

| | | |
|---|---|---|
| 2008/0262427 A1 | 10/2008 | Hommann |
| 2010/0312195 A1* | 12/2010 | Johansen ............ A61M 5/2033 604/192 |
| 2011/0313364 A1 | 12/2011 | Rolfe et al. |
| 2012/0004640 A1 | 1/2012 | Rosen et al. |
| 2012/0220954 A1* | 8/2012 | Cowe ................. A61M 5/2033 604/228 |
| 2013/0096512 A1 | 4/2013 | Ekman et al. |
| 2013/0274655 A1 | 10/2013 | Jennings et al. |

FOREIGN PATENT DOCUMENTS

| | | |
|---|---|---|
| JP | 2012513855 A | 6/2012 |
| WO | 2009062508 A1 | 5/2009 |
| WO | 2010077280 A1 | 7/2010 |
| WO | 2012000939 A1 | 1/2012 |
| WO | 2012085031 A1 | 6/2012 |

\* cited by examiner

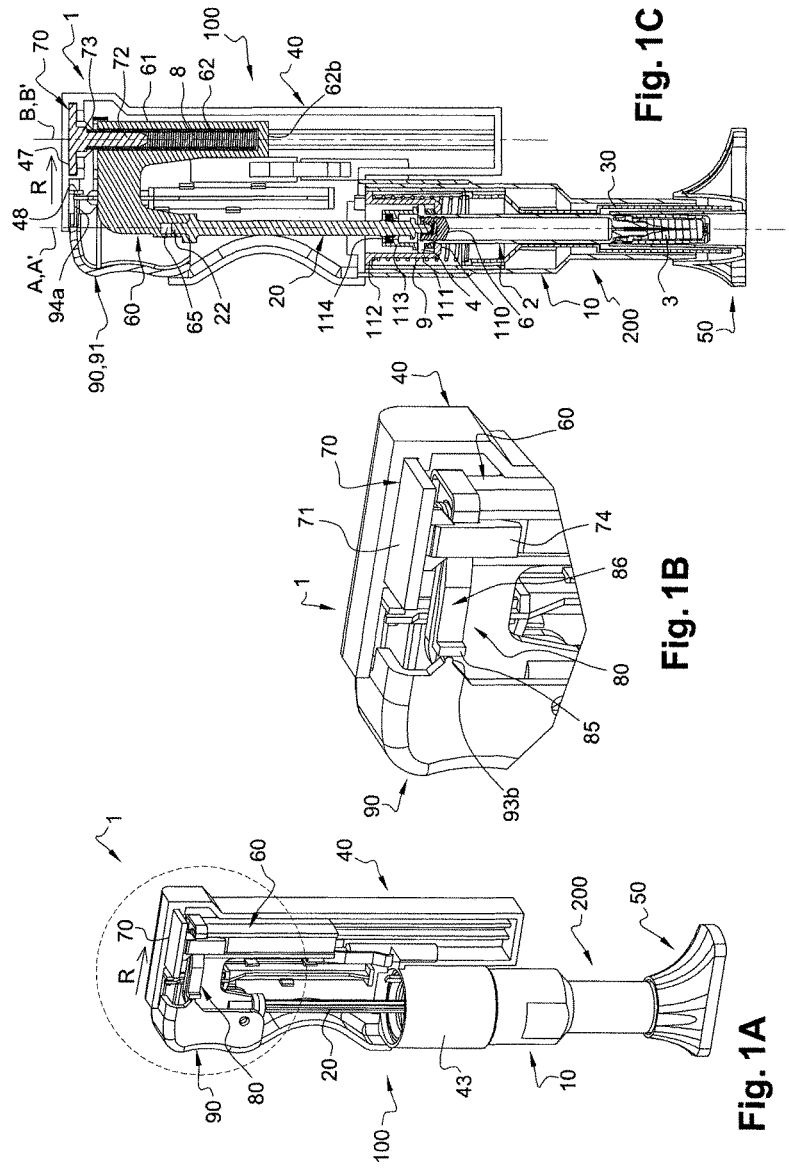

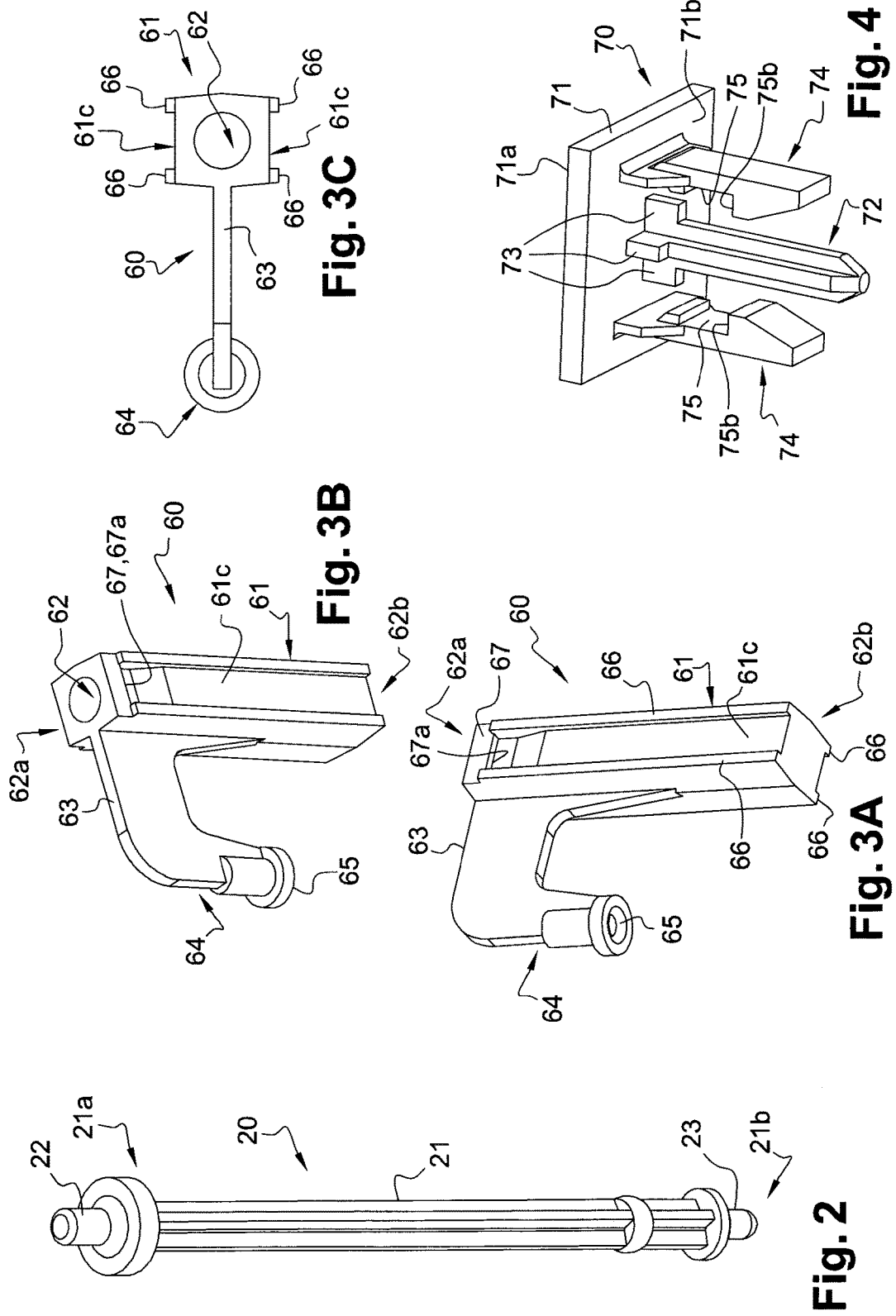

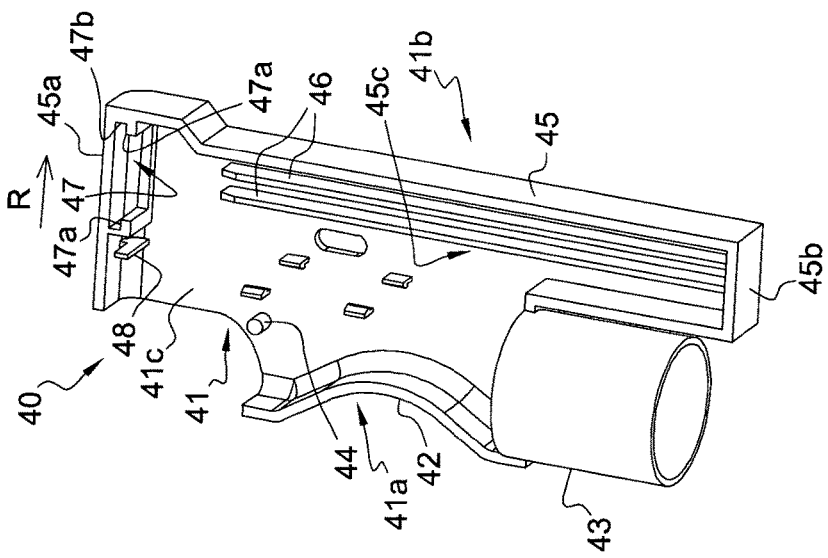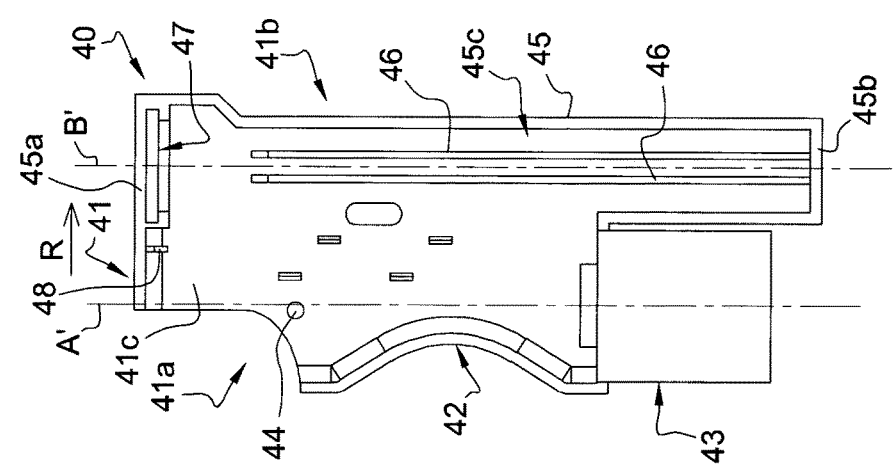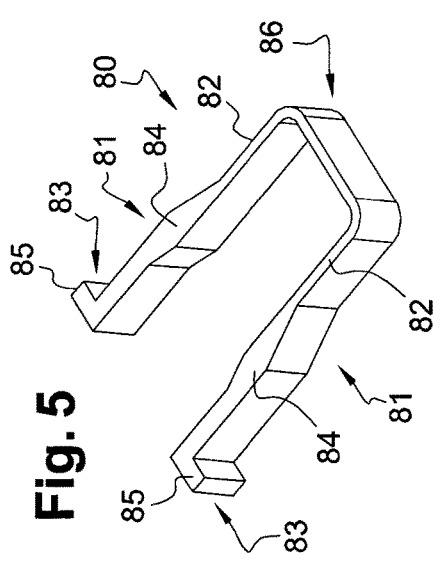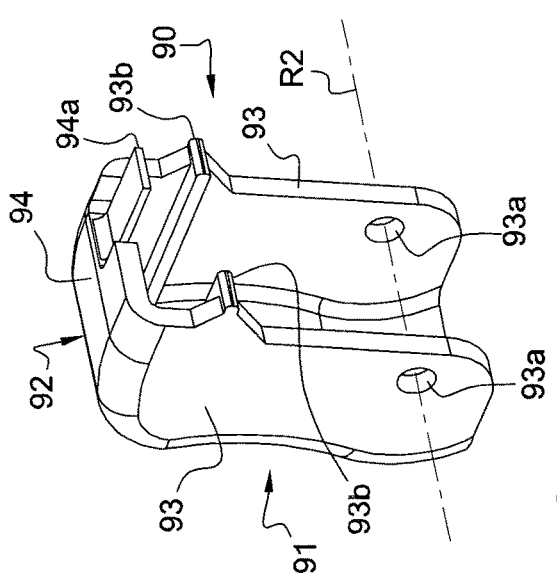

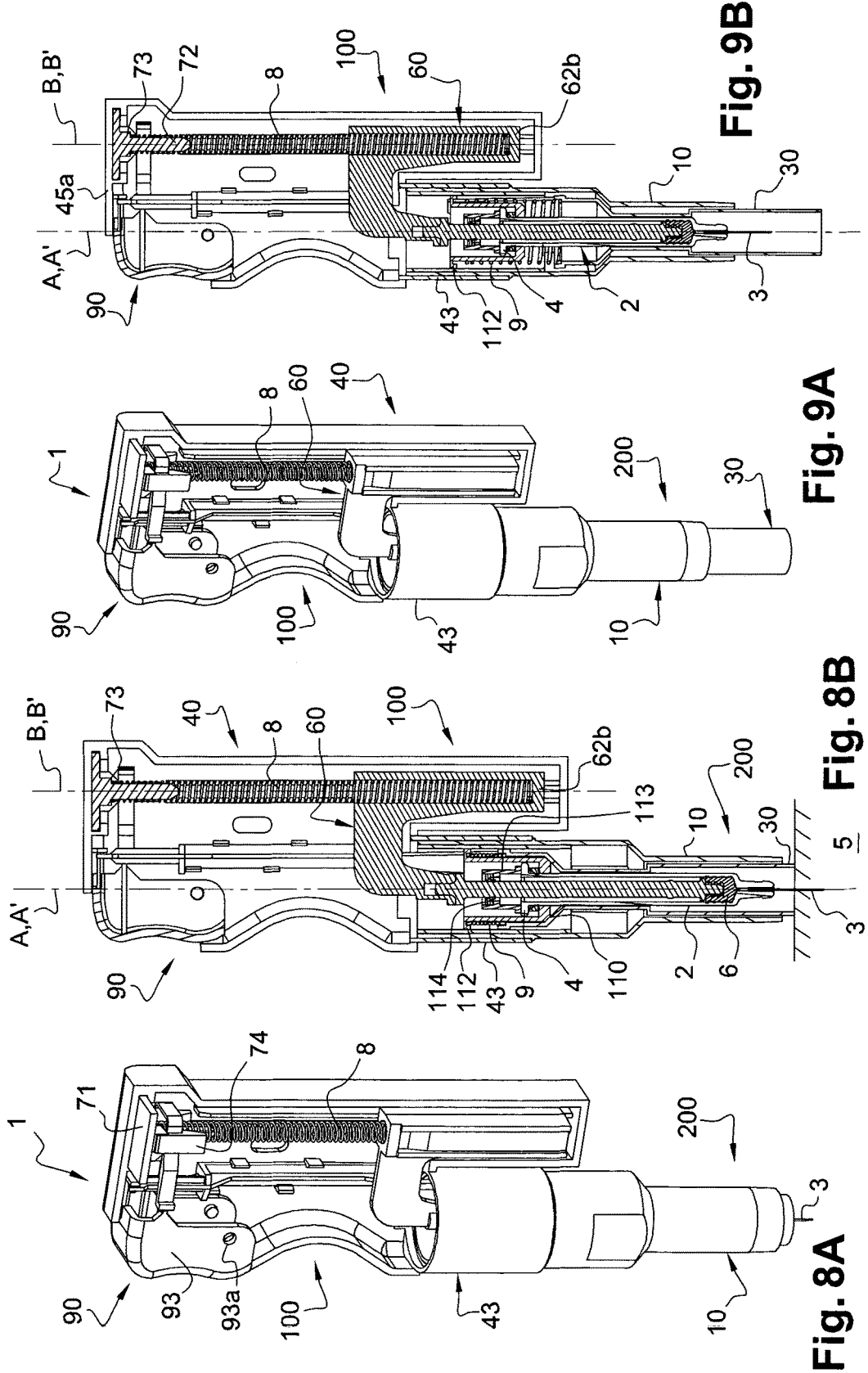

AUTOMATIC INJECTION DEVICE

CROSS-REFERENCE TO RELATED APPLICATIONS

This application is the United States national phase of International Application No. PCT/IB2014/000845 filed May 22, 2014, and claims priority to European Patent Application No. 13305679.6 filed May. 24, 2013, the disclosures of which are hereby incorporated in their entirety by reference.

The present invention relates to a device for injection of a product, for which the insertion step of the needle is automated and may be completed with minimal effort from the user.

In this application, the distal end of an element or of a device means the end furthest away from the hand of the user and the proximal end means the end closest to the hand of the user, when the element or device is in the use-position. Similarly, in this application, the terms "in the distal direction" and "distally" mean in the direction of the injection, and the terms "in the proximal direction" and "proximally" mean in the direction opposite to the direction of injection.

Devices for automatic injection of a product, also called autoinjectors, are widely used in medical fields where the treatment of a pathology requires daily injections, such as the treatment of some diabetes or arthritis, and where patients often proceed to these injections on their own. As patients are not professional healthcare workers, the whole process is as much as possible automated so that the patient needs not make decisions during the injection. Autoinjectors usually comprise on one hand a container having a needle and filled with the product to be injected, such as a prefilled syringe for example or a cartridge, and on the other hand a motor part, in other words a part comprising the various systems which will trigger the insertion of the needle, realise the injection and potentially activate a protection system at the end of injection.

Most of the already existing autoinjectors comprise at least a system for automatically inserting the needle into the patient's skin, and triggering means for initiating such an insertion of the needle, the triggering means being intended to be activated by the patient when he is ready. Nevertheless, most of the automatic insertion systems of the autoinjectors of the prior art require substantial effort from the user for completing such a triggering step. For example, those automatic insertion systems may involve deflection of one or more flexible parts of the autoinjector, or they may imply overcoming a resisting force between two parts of the autoinjector, in such a way that the patient needs to apply a high force on the autoinjector at the time he wishes to activate the triggering means, while the autoinjector is bearing on the skin of the patient. The high force necessary for activating the triggering means may hurt the user's skin. It may also cause the user to be reluctant to proceed to the injection, or to be puzzled, not knowing if he should continue the injection or not. In some cases, the force required for initiating the injection may be too high for users having difficulties for manipulating devices.

It is therefore important that at least the insertion of the needle into the injection site, which is the first step to take place in the injection process, be simplified and proceed softly and smoothly with no opportunity for the user to face anxiety. In this view, it is important that the user needs not apply too high a force on the device at the time he is ready to activate the triggering means for proceeding to the insertion step of the needle into the site of injection.

In addition, many autoinjectors of the prior art are designed so that the container, such as a syringe for example, is assembled into the device during the manufacture of the motor part, pieces of the motor part and of the container being connected together in an intricate way. Proceeding this way means that, once a motor part is designed for a syringe of a certain volume capacity and prefilled with a specified drug, it is not possible to use the same motor part for another type of container or for another drug, as it has been designed to fit with the specific shape of the syringe.

Nevertheless, for the pharmaceutical companies, it would be advantageous to prepare on one hand the prefilled syringe, and on the other hand the motor part of the autoinjector, and then assemble the prefilled syringe onto the motor part of the autoinjector, without having to redesign the motor part each time the type of syringe is changed or each time the drug is replaced by another drug with different properties, for example with a different viscosity.

Autoinjectors have been proposed, for which at least a part of the motor part is positioned laterally with respect to the syringe.

Nevertheless, such autoinjectors still need to be improved with regards to the intensity of the force the user needs to apply on the device at the time of triggering the insertion of the needle.

In addition, as mentioned before, as users of these autoinjectors are usually not professional healthcare workers, it is desirable that such devices have a high reliability, and that not only the insertion step, but the whole process of the injection, from insertion of the needle into the injection site to withdrawal of the device from the injection site and disposal of the device proceeds softly and smoothly with no opportunity for the user to face anxiety.

A first aspect of the invention is a device for injection of a product into an injection site, said device comprising:

a housing having a longitudinal axis A and receiving a container for the product to be injected, said container being aligned on said longitudinal axis A, said container being substantially closed at a proximal end by a stopper, said stopper being capable of being moved distally within said container so as to expel the product to be injected, and at a distal end by a needle for the exit of the product to be injected, said container being movable with respect to said housing between a first position, in which the needle does not extend beyond a distal end of the housing, and a second position, distally spaced with respect to said first position, in which the needle extends beyond the distal end of the housing, biasing means, coupled to said housing and designed for producing a distal force along a longitudinal axis B when going from a first state to a second state, said second state being less stressed than said first state, said longitudinal axis B being laterally spaced with respect to said longitudinal axis A along a transversal direction R, linking means for coupling said biasing means to said container at least from said first position to said second position of the container, said linking means being shaped and dimensioned so as to transmit said distal force to said container when said biasing means goes from its first state to its second state so as to move said container from its first position to its second position, retaining means coupled to said container and to said housing in the first position of the container, for releasably maintaining said biasing means in its first state, said retaining means being capable of moving from a passive condition, in which it maintains said biasing means in its first state, to an active condition, in which said biasing means is free to expand to its second state, wherein the device further comprises deactivating means coupled to said retaining means, capable of moving with respect to the retaining means from a first position, in which said retaining means is in its passive condition, to a second position, offset from said first position along said transversal direction R, in which said retaining means is in its active condition, triggering means for moving said deactivating means from its first position to its second position.

In the present application, longitudinal axis A and B are both aligned on the distal-proximal direction: in other words longitudinal axis A and B are parallel to each other but they are separate and laterally spaced from each other. As will appear later in the description, such a location of the biasing means allows the device of the invention to be manufactured in two steps.

The arrangement of the device of the invention allows a patient to proceed to the insertion step of the needle with no substantial effort: indeed, as will appear from the description below, the fact that the deactivating means need to be moved along a transversal direction with respect to the longitudinal axis A, requires only little effort from the user. Contrary to the autoinjectors of the prior art, thanks to the arrangement of the deactivating means in a transversal plane of the longitudinal axis A of the container, the cooperation of the deactivating means with the triggering means for freeing the retaining means, and thus the biasing means, require only little force. The step for freeing the retaining means therefore does not require that the device of the invention be applied with a high force on the skin of the patient at the time of activation of the triggering means in order to initiate the insertion of the needle.

In particular, because of the arrangement of the retaining means of the device of the invention requiring little effort for initiating the insertion step, it is possible to provide the device of the invention with biasing means having a high force. Indeed, thanks to the arrangement of the retaining means of the device of the invention, the effort required for beginning the insertion step will remain the same regardless from the intensity of the force of the biasing means. Moreover, in the embodiments in which the biasing means also serve for pushing distally the stopper, via a plunger for example, during the injection step, it is possible to provide the device with biasing means showing a high intrinsic force. For example, when the product to be injected shows a high viscosity, the device of the invention may be provided with biasing means having a high intrinsic force allowing said biasing means to automatically realize both the insertion step and the injection step, while the effort required from the user at the beginning of the process in order to initiate the insertion step remains low.

In embodiments, said retaining means comprising legs capable of deflecting radially with respect to longitudinal axis B between a locked position, in which the retaining means is in its passive condition, to a free position in which the retaining means is in its active condition, said deactivating means comprise cooperating surfaces, said cooperating surfaces causing said legs to move from their locked position to their free position when said deactivating means is moved from its first position to its second position along radial direction R.

For example, the linking means comprise at least a linking member aligned on said transversal direction R, said linking member connecting said biasing means to said container.

In embodiments, said biasing means being a helical spring and said device further comprising a plunger rod for distally pushing said stopper within said container during an injection step, said linking member is connected to said container via said plunger rod, said linking member further comprising a tubular lodging receiving said helical spring, said helical spring being in distal abutment on a distal transversal wall of said tubular lodging and being in proximal abutment on a proximal transversal wall fixed with respect to said housing.

The triggering means may be actionable by the user. In embodiments, the triggering means comprises a button mounted in pivoting relationship with respect to said housing, said button comprising a pushing surface accessible to a user for pivoting said button, said button further comprising an actuating surface capable of cooperating with a surface of said deactivating means, for moving said deactivating means from its first position to its second position, when the button is caused to pivot.

In embodiments, the device further comprises:

locking means for preventing said triggering means from moving said deactivating means from its first position to its second position, said locking means being releasable, and releasing means for releasing the locking means.

The device of the invention is therefore very safe as it cannot be triggered before the user has neutralized the security system formed by the releasable locking means.

In embodiments, the locking means comprise a movable surface of said device, said surface being movable between a first position, in which it prevents cooperation between said deactivating means and said button, to a second position, in which it allows cooperation between said deactivating means and said button. The movable surface may be moved from its first position to its second position by action of the user, for example, when the user applies the device on the skin of the patient.

In embodiments, the device further comprises urging means coupled to said stopper and to said housing when said container is in its second position, said urging means being designed for distally moving said stopper when going from a first state to a second state, said second state being less stressed than said first state, thereby realizing injection of the product.

The device of the invention is therefore entirely automated, as both the insertion step and the injection step are automatically completed by means of the biasing means and of the urging means. The user is therefore ensured that these two steps proceed optimally, as he does not have to manually complete them.

In embodiments, said helical spring being further capable of going from its second state to a third state, during which said spring moves the stopper distally, said third state being less stressed than said second state, said helical spring forms both said biasing means and said urging means.

Such an embodiment allows to manufacture a compact device as only one spring is required for automatically performing two steps, namely an insertion step, during which the needle is inserted into the injection site, and an injection step, during which the product to be injected is actually delivered to the injection site. Alternatively, the helical spring may be a concentric double helical spring having a high intrinsic force, adapted for completing the injection step of a viscous product.

In embodiments, the device further comprises:

needle protection means, at least partially received within said housing, and movable with respect to said container when said container is in its second position with respect to said housing, between an insertion position, in which a distal tip of the needle extends beyond the distal end of the needle protection means, and a final position, in which the distal tip of the needle does not extend beyond the distal end of the needle protection means, and elastic return means, coupled to said needle protection means and to said container, and designed for automatically moving said needle protection means from its insertion position to its final position, upon removal of the device from an injection site by a user.

The device of the invention therefore requires no particular effort from the user, is of simple use and perfectly safe: once the needle has been inserted into the injection site, as soon as the user withdraws the device from the injection site, the needle protection is activated, and the needle is immediately rendered inaccessible to the user. In addition, in case the user misuses the device and withdraws it from the injection site before the injection is actually completed, the needle protection is nevertheless activated. Actually, as soon as the needle is inserted in the injection site, the removal of the device from the injection will automatically activate the needle protection. The device of the invention is therefore very comfortable for the user, in particular where the user is not a professional healthcare worker, as the user knows that the used needle will never come in contact with his hand or fingers, regardless of how he performs the injection step.

The device of the invention may be formed from two autonomous parts, a motor part and a housing part.

For example, a motor part of the device, comprising the biasing means, the linking means, the retaining means, the deactivating means, the triggering means and optionally the urging means may be assembled, on one hand. On another hand, the housing part may be assembled separately, said housing part comprising the housing receiving the container, and optionally the needle protection means and the elastic return means. Each part, namely the motor part on one hand and the housing part on the other hand, is autonomous before it is connected to the other part, and may be transported and/or handled on its own. This allows pharmaceutical companies for example to prefill the container, for example a syringe, of the housing with the drug to be injected on a first site, and then to assemble the motor part later on. In particular, thanks to the arrangement of the device of the invention, it is not necessary to redesign the motor part each time the type of container, for example a syringe, is changed or each time the drug is replaced by another drug with different properties, for example with a different viscosity.

In embodiments, the device of the invention is under the form of two autonomous connectable parts, namely a motor part and a housing part, said motor part comprising at least the biasing means, the linking means, the retaining means, the deactivating means, the triggering means and optionally the urging means, said housing part comprising at least said housing receiving the container, and optionally the needle protection means and the elastic return means, said device further comprising connecting means for connecting said motor part to said housing part at time of use.

As seen above, the arrangement of the various parts of the device of the invention, and in particular the fact that the biasing means and optionally the urging means are located laterally with respect to the longitudinal axis of the housing, allow to treat, transport, and/or handle the motor part on one hand, and the housing part on the other hand, before connecting these two parts. This is advantageous for pharmaceutical companies which fill the container of the housing independently from the motor part. In addition, thanks to the arrangement of the device of the invention allowing said device to be under the form of two connectable parts, it is not necessary to redesign the motor part each time the type of syringe/container is changed or each time the drug is replaced by another drug with different properties.

The present invention will now be described in greater detail based on the following description and the appended drawings in which:

FIGS. 1A-1F are respectively a perspective view, a partial perspective view at a greater scale, a longitudinal section view, a partial longitudinal section and perspective view, a partial section and perspective view at a greater scale and a transversal section view of the device of the invention in a before use position where the retaining means are still in their passive condition, FIG. 2 is a perspective view of the plunger rod of the device of FIG. 1A-F, FIGS. 3A-3C are views of the linking member of the device of FIG. 1A-F, respectively a perspective view from the bottom, a perspective view from the top, and a top view, FIG. 4 is a perspective view from the bottom of the retaining means of the device of FIG. 1A-F, FIG. 5 is a perspective view from the top of the deactivating means of the device of FIG. 1A-F, FIG. 6 is a perspective view of the triggering means of the device of FIG. 1A-F, FIGS. 7A-B are respectively a front view and a perspective view of a holder of the motor part of the device of FIG. 1A-F, FIGS. 8A-B are respectively a perspective view and a longitudinal section view of the device of FIG. 1A-F, once the triggering means have been activated, and the biasing means have completed both an insertion step and an injection step, FIGS. 9A-B are respectively a perspective view and a longitudinal section view of the device of FIG. 1A-F, once the needle protection means has reached its final position.

With reference to FIGS. 1A-1F, is shown a device 1 of the invention comprising:

a syringe 2 having a longitudinal axis A, the syringe comprising a needle 3, a stopper 6, and being filled with a product 7, a housing 10, a plunger rod 20, a needle protection sleeve 30, a holder 40, a first helical spring 8 aligned on a longitudinal axis B laterally spaced from the longitudinal axis A along a transversal direction shown by the arrow R, a protection cap 50, a linking member 60 for linking the plunger rod 20 to the first helical spring 8, a retaining piece 70, a deactivating member 80, a button 90, a second helical spring 9, aligned on longitudinal axis A.

With reference to FIGS. 1A-7B, the different parts of the device 1 will now be described in details.

The syringe 2 has the global shape of a tube substantially closed at its distal end by a needle 3 for the exit of the product to be injected, and opened at its proximal end, where it is provided with an outer flange 4. As shown on FIG. 1C, the syringe 2 is prefilled with the product 7 to be injected and is closed at its proximal end by a stopper 6. As will appear in the following description, the stopper 6 is capable of moving within the syringe 2 under distal pressure and is intended to cooperate with the distal end of the shaft 21 (see FIG. 2) of the plunger rod 20 in order to realize injection of the product 7.

The outer flange 4 of the syringe 2 is snap-fitted into a syringe holder 110, fixed with respect to the syringe 2, and forming a sleeve 111 extending in the proximal direction. The proximal end of the sleeve 111 is provided with an outer rim 112.

The syringe 2 is partially received within the needle protection sleeve 30. The needle protection sleeve 30 has the global shape of a tube and is movable with respect to the syringe 2 between a proximal position, in which the needle 3 extends beyond the distal end of the needle protection sleeve 30 (insertion step and injection step, see FIGS. 8A-B), and a distal position, in which the needle 3 does not extend beyond the distal end of the needle protection sleeve 30 (final position, see FIGS. 9A-B). The needle protection sleeve 30 is coupled to the syringe 2 by means of the second helical spring 9. As shown on FIG. 1C, the proximal end of the second helical spring 9 is in abutment against a distal face of the outer rim 112 of the sleeve 111 of the syringe holder 110, and the distal end of the second helical spring 9 is in abutment against the proximal end of the needle protection sleeve 30. In its distal position as shown on FIGS. 9A-B, the needle protection sleeve 30 covers the needle 3 so that it may not be reached by a user and so that accidental needlesticks are avoided.

With reference to FIGS. 1A-F, the housing 10 has the global shape of a tube. It is maintained fixed with respect to the holder 40 by fixation means, such as snap-fitting means (not shown). The housing 10 is dimensioned and shaped so as to be able to receive a container, the syringe 2 on the example shown, for the product 7 to be injected. On the example shown, the housing 10 further receives the syringe holder 110 and the needle protection sleeve 30. The syringe 2 is coupled to the housing 10 via the plunger rod 20 being coupled to the holder 40 by means of first helical spring 8, as will be described below. The syringe 2 is therefore movable with respect to the housing 10 between a first position, in which the needle 3 does not extend beyond a distal end of the housing 10 (as shown on FIG. 1C), and a second position, distally spaced with respect to said first position, in which the needle 3 extends beyond the distal end of the housing 10 (see FIGS. 8A and 8B).

With reference to FIGS. 1A-F, the stopper 6 is connected to the plunger rod 20. With reference to FIG. 2, the plunger rod 20 comprises a shaft 21 dimensioned so as to be able to be received within the syringe 2, and provided with a proximal plug 22 at its proximal end 21a and with a distal plug 23 at its distal end 21b. As shown on FIG. 1C, the plunger rod 21 is aligned on the longitudinal axis A and the distal plug 23 is connected to the stopper 6.

With reference to FIG. 1C, the syringe holder 110 is further provided with an inner sleeve 113 surrounding the distal region of the plunger rod 20. The inner sleeve 113 is provided with a transversal rubber part 114 which is in contact with the distal part of the shaft 21 of the plunger rod 20. This rubber part 114 forms a releasable locking means of the translational movement of the plunger rod 20 with respect to the syringe 2. Indeed, a distal pressure applied on the plunger rod 20 will not cause distal movement of the plunger rod 20 within the syringe 2 as long as said distal pressure is not greater than the friction force present between the plunger rod 20 and the syringe 2, said friction force being provided by said rubber part 114 being in contact with the shaft 21 of the plunger rod 20.

With reference to FIG. 1C, the proximal plug 22 of the plunger rod 20 is connected to the linking member 60.

With reference to FIGS. 3A-C, the linking member 60 will now be described in detail. The linking member 60 has the global shape of a reversed U: one leg of the U comprises a longitudinal body 61 receiving a tubular lodging 62 open at its proximal end 62a and closed at its distal end 62b. The tubular lodging 62 is shaped and dimensioned so as to receive therein the first helical spring 8, as shown on FIG. 1C. In its proximal region, the longitudinal body 61 is provided with a lateral extension, under the form of a bridge 63 linking the longitudinal body 61 to the second leg of the U, namely a distal projection 64 provided at its distal end with a recess 65. The longitudinal body 61 is provided on each of its side walls 61c with a pair of outer longitudinal ridges 66. Each side wall 61c is further provided at its proximal end with an outer rim 67 forming a proximal surface abutment 67a.

As shown on FIG. 1C, the plunger rod 20 is connected to the linking member 60 by means of its proximal plug 22 being friction forced inside the recess 65 of the linking member 60.

With reference to FIG. 4, the retaining piece 70 will now be described in detail. The retaining piece 70 comprises a globally square shaped plaque 71 having a proximal face 71a and a distal face 71b. The distal face 71b is provided in its center with a shaft segment 72 extending in the distal direction. The shaft segment 72 is provided at its junction with the distal face 71b with a plurality of circumferentially distributed radial rims 73, three of them being visible on FIG. 4. The distal face 71b of the plaque 71 is further provided with two lateral flexible legs 74 extending in the distal direction, capable of being radially deflected with respect to the longitudinal axis of the shaft segment 72. Each lateral flexible leg 74 is provided, on its wall facing the shaft segment 72, with a radial recess 75 forming a distal abutment surface 75b.

With reference to FIG. 1C, the shaft segment 72 of the retaining piece 70 is dimensioned and shaped so as to be capable to be received within the proximal region of the inner space of the first helical spring 8.

With reference to FIG. 5, the deactivating member 80 is a U-shaped body 86, each branch 81 of the U being provided with a thin wall 82, in its part opposed to its free end 83, and with a thick wall 84 in its part close to to its free end 83. Each free end 83 is further provided with an outer transversal rim 85.

With reference to FIG. 6, the button 90 will now be described in detail. The button 90 has the global shape of a cap 91: the cap 91 is provided with a pivoting part 92 rotatable around an axis R2. The pivoting part 92 comprises two parallel longitudinal lateral walls 93, provided with throughholes 93a for accomodating a pivot (see FIG. 8A). The two lateral walls 93 extend in a radial direction with respect to axis R2 and are linked to each other at their free ends by a bridging wall 94. Each lateral wall 93 has a globally rectangular shape and is further provided with a protruding surface 93b. The bridging wall 94 is also provided with a projection 94a protruding in the same direction as the protruding surfaces 93b of the lateral walls 93.

With reference to FIGS. 7A-B, the holder 40 will now be described in detail. The holder 40 has the global shape of a back wall 41 defining two longitudinal parts laterally spaced from each other, namely a first longitudinal part 41a having a longitudinal axis A', intended to be aligned on the longitudinal axis A of the syringe 2 (see FIG. 1C), and a second longitudinal part 41b, having a longitudinal axis B', intended to be aligned on the longitudinal axis B of the helical spring 8 (see FIG. 1C). Longitudinal axis A' and B' are laterally spaced from each other along a transversal direction shown by the arrow R.

In its first longitudinal part 41*a*, the back wall 41 is provided with a partial side wall 42 having a curved shape, and defining an inner face 41*c* of back wall 41. From the distal end of the side wall 42, extends a tubular sleeve 43 open at both ends, the tubular sleeve 43 being aligned on the longitudinal axis A'. As will appear from the description below, the tubular sleeve 43 is dimensioned and shaped so as to be capable to receive the housing 10 (see FIG. 1C). In the proximal region of the first longitudinal part 41*a*, the inner face 41*c* of the back wall 41 is provided with a transversal pivot 44.

In its second longitudinal part 41*b*, the back wall 41 is provided with a side wall 45 facing partial side wall 42. Side wall 45 is provided at its proximal end with a proximal transversal wall 45*a* and at its distal end with a distal transversal wall 45*b*, both extending laterally towards first longitudinal part 41*a* and thereby defining with the side wall 45*a* longitudinal open lodging 45*c* aligned on longitudinal axis B'. The second longitudinal part 41*b* is further provided with a pair of two longitudinal ridges 46 extending from the inner face 41*c* of back wall 41 inside the open lodging 45*c*.

As shown on FIG. 7B, the proximal transversal wall 45*a* is provided on its distal face with a transversal lodging 47 aligned on longitudinal ridges 46 and on longitudinal axis B'. The transversal lodging 47 is provided with distal transversal rims forming distal abutment surfaces 47*a* and transversal abutment surfaces 47*b* in the direction R. In addition, the proximal transversal wall 45*a* is further provided on its distal face with a distal peg 48, laterally spaced with respect to transversal lodging 47 in the direction of first longitudinal part 41*a*.

The device 1 of the invention may be provided to the user as shown on FIGS. 1A-F. Anyway, the device 1 may be manufactured by assembling two autonomous parts, hereinafter called the motor part 100 on one hand, and the housing part 200 on the other hand.

Figure 1F:
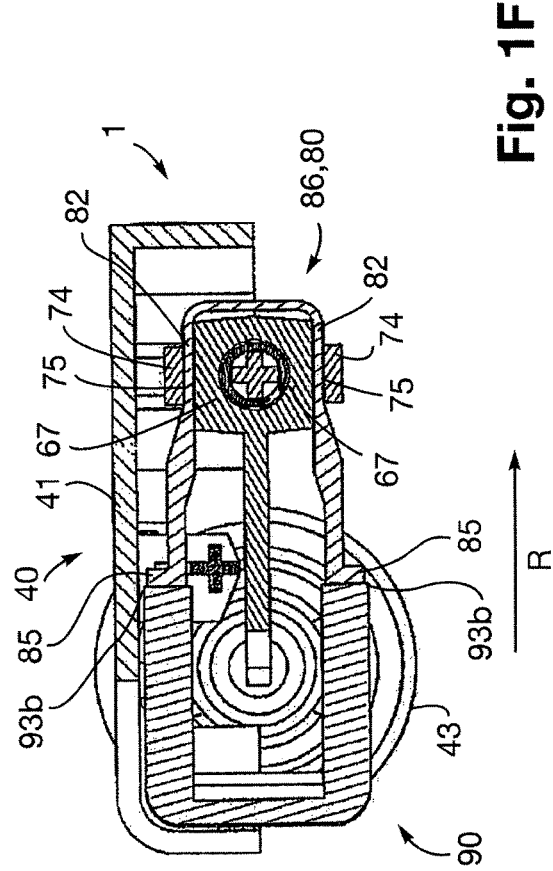
Figure 1D:
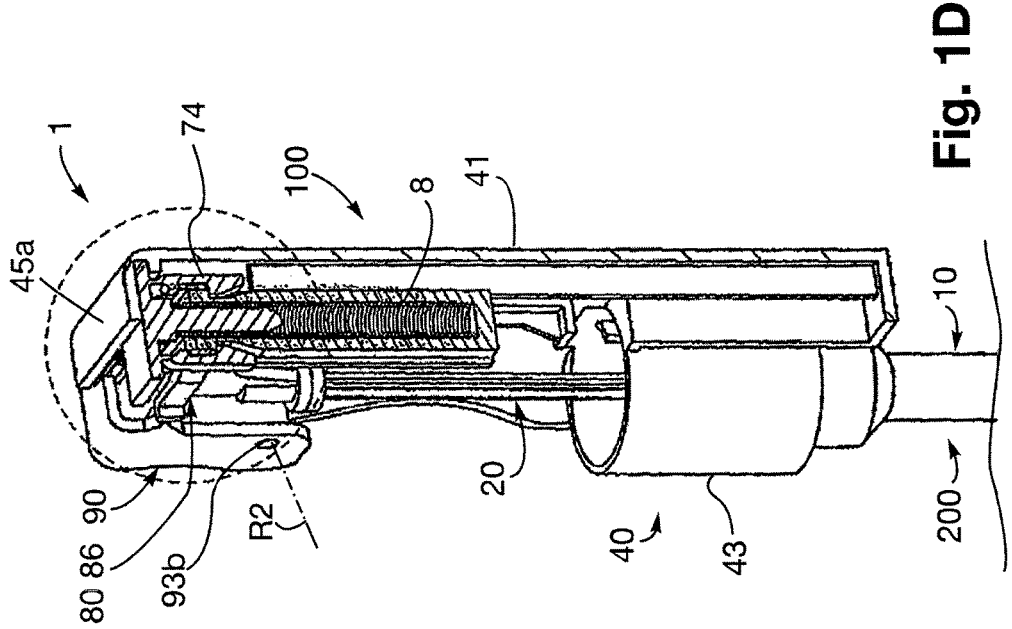

With reference to FIGS. 1A-F, the motor part 100 comprises the following elements: the holder 40, the first helical spring 8, the linking member 60, the retaining piece 70, the deactivating member 80 and the button 90. Within this motor part 100, and in the before use position of the device 1 as shown on FIGS. 1A-F, the linking member 60 and the holder 40 are coupled to each other via the first helical spring 8 and the retaining piece 70. The first helical spring 8 is received within the tubular lodging 62 of the linking member 60, with the distal end of the helical spring 8 bearing on the transversal wall closing the distal end 62*b* of the tubular lodging 62. The segment shaft 72 of the plaque 71 is received within the proximal region of the inner space of the first helical spring 8, so that the proximal end of the first helical spring 8 bears on the distal faces of the radial rims 73 of the retaining piece 70. With reference to FIGS. 1C-E, the plaque 71 is received within the transversal lodging 47 of the holder 40. The plaque 71 is therefore blocked in longitudinal translation with respect to the holder 40, in the proximal direction by the proximal transversal wall 45*a*, and in the distal direction by the distal abutment surfaces 47*a* of the transversal lodging 47. The plaque 71 is further blocked in transversal translation along direction R with respect to the holder 40, by means of transversal abutment surfaces 47*b*.

In addition, with respect to FIG. 1E, the outer rims 67 of the side walls 61*c* of the linking member 60 are engaged in the radial recesses 75 of the flexible legs 74 of the retaining piece 70, with the proximal surface abutments 67*a* of these outer rims 67 being in distal abutment against the distal abutment surfaces 75*b* of the radial recesses 75.

As a consequence, the first helical spring 8, which is in a first stressed state on FIGS. 1A-F, is not allowed to expand, as it is maintained in this first stressed state by means of outer rims 67 being engaged in radial recesses 75.

The two longitudinal ridges 46 of the holder 40 are engaged in the inner space formed by the pair of outer longitudinal ridges 66 of the longitudinal body 61 of the linking member 60. As will appear from the description below, the two longitudinal ridges 46 of the holder 40 will form guiding means for the the distal translation of the linking member 60 during the insertion step and injection step.

With reference to FIGS. 1B, and 1D-1F, the U-shaped body 86 of the deactivating member 80 is located around the longitudinal body 61 of the linking member 60, so that the outer rims 67 of the longitudinal body 61 are received within the inner space of the U-shaped body 86, with the thin walls 82 of the U-shaped body 86 being sandwiched between the radial recesses 75 of the flexible legs 74 of the retaining piece 70 and the outer rims 67 of the linking member 60 (see FIGS. 1E and 1F).

As shown on FIGS. 1B and 1F, in the before use position of the device 1, the outer transversal rims 85 of the U-shaped body 86 of the deactivating member 80 face the protruding surfaces 93*b* of the button 90. In this position, the button 90 is pivotingly mounted onto the holder 40 by means of pivot 44 of the holder 40 being engaged in one throughole 93*a* of the button 90 (see FIG. 8A). The button 90 is therefore able to pivot around axis R2 (see FIG. 1D).

All the elements forming the motor part 100, namely the holder 40, the first helical spring 8, the linking member 60, the retaining piece 70, the deactivating member 80 and the button 90, are linked together or coupled to each other by the relationships described above and therefore form an autonomous part, that can be handled on its own.

With reference to FIGS. 1A-F, the housing part 200 comprises the following elements: the syringe 2 and its syringe holder 110, the housing 10, the plunger rod 20, the needle protection sleeve 30, the second helical spring 9, and the protection cap 50. All these elements are also coupled together so as to form an autonomous part that may be handled on its own. As a consequence, the syringe 2 may be filled at the premises of pharmaceutical companies and then assembled at a later stage to the motor part 100.

The housing part 200 is assembled to the motor part 100 by engaging the proximal end of the plunger rod 20 through the distal open end of the tubular sleeve 43 of the holder 40, and moving the housing part 200 proximally until the proximal plug 22 of the plunger rod 20 gets stuck into the recess 65 of the linking member 60, as shown on FIG. 1C. The proximal plug 22 of the plunger rod 20 and the recess 65 of the linking member 60 therefore form part of connecting means for connecting the motor part 100 to the housing part 200 at time of use. As mentioned above, the connecting means may further comprise fixation means such as snap-fitting means (not shown) for connecting in particular the holder 40 to the housing 10. The device 1 is therefore assembled and is ready to be used. The device 1 is provided to the user in its assembled configuration, as shown on FIGS. 1A and 1C, with the cap 50 protecting the needle 3 of the syringe 2.

The housing 10 is therefore fixed in longitudinal and transversal translation with respect to the holder 40: as a consequence, in the assembled configuration of the device 1, all the elements from the motor part 100 which were described to be fixed with respect to the holder 40 are also fixed with respect to the housing 10.

The operation of the device 1 of the invention will now be explained with reference to FIGS. 1A-9B.

For proceeding to an injection, the user removes the cap 50. The various relationships described above between the various elements forming the motor part 100 and the housing part 200 are not changed by the removal of the cap 50.

In embodiments, the device 1 comprises locking means for preventing the device 1 to be triggered if it is not correctly positioned on the skin of the patient.

In this view, with reference to FIG. 1C, the projection 94a is in abutment against the distal peg 48 of the proximal transversal wall 45a of the housing 40. As a consequence, pushing on the cap 91 in the transversal direction R will not trigger the insertion step as pivoting movement of the button 90 is prevented by distal peg 48. In order to free the projection 94 from the distal peg 48, the user needs to apply the distal end of the device 1 on the skin of the patient and exert a distal pressure on the proximal transversal wall 45a so as to slightly move the needle protection means 30 with respect to the holder 40: such a step is known from devices of the prior art and is not described in the present application.

Once the device 1 has been applied on the patient's skin and the locking means under the form of peg 48 have been released, the user may trigger the insertion step by applying a pressure on the cap 91 of the button 90 so as to pivot its pivoting part 92 with respect to axis R2. Due to the shape and dimensions of the button 90, this pivoting results in protruding surface 93b applying a transversal force, along the transversal direction R, on the outer transversal rims 85 of the deactivating member 80 (see FIG. 1F).

Only little force is required from the user for pushing cap 91. In addition, as the force exerted on the deactivating member is a transversal force, the user needs not apply the device onto the skin with a high force. The device 1 is therefore simple to use and does not create a bad feeling on the skin of the patient. The force required to be applied to trigger the insertion step neither hurts the patient. Because only low force is required from the user to perform this step, the device 1 may be used by people having difficulties for handling objects in their hands.

The activation of the triggering means and the initiation of the insertion step of the needle is therefore very easy and simple: the user has no anxiety to face as the step proceeds very softly and smoothly.

Under the effect of the transversal force exerted on the outer transversal rims 85 of the deactivating member 80, the deactivating member 80 as a whole moves in the transversal direction R. Nevertheless, as both the linking member 60 and the retaining piece 70 are fixed with respect to the holder 40, as described above, the outer rims 67 of the linking member 60 and the flexible legs 74 of the retaining piece 70 remain fixed in translation in the transversal direction R with respect to the deactivating member 80. As a consequence, the U-shaped body 86 moves in the transversal direction R with respect to both the outer rims 67 and the flexible legs 74. The thick walls 83 move in the transversal direction R and become sandwiched between the outer rims 67 and the flexible legs 74. As the thick walls 83 are thicker than the thin walls 82, their movement causes the flexible legs 74 to deflect outwardly radially with respect to the longitudinal axis of the shaft segment 72, which is aligned on longitudinal axis B. As a consequence, the distal abutment surfaces 75b of the radial recesses 75 of the flexible legs 74 escape from the proximal surface abutments 67a of the outer rims 67 of the linking member 60.

The first helical spring 8 is therefore released and expands in order to go to a second state less stressed than its first state.

The button 90 therefore acts as triggering means for releasing the retaining means, namely the flexible legs 74. While expanding, the first helical spring 8 produces a distal force along longitudinal axis B and causes distal movement of the linking member 60 which is no more fixed with respect to the holder 40. The two longitudinal ridges 46 of the holder 40, which are engaged in the inner space formed by the pair of outer longitudinal ridges 66 of the longitudinal body 61 of the linking member 60, form guiding means for the distal translation of the linking member 60 during this insertion step of the needle 3.

In addition, the linking member 60, in particular thanks to its bridge 63 and its distal projection 64, transmits this distal force to the plunger rod 20 of the syringe 2. Because of the friction force present between the shaft 21 of the plunger rod 20 and the syringe 2, provided by the presence of the rubber part 114 as described above and because of the gliding resistance of the stopper 6 along the inner walls of the syringe 2, neither the plunger rod 20 nor the stopper 6 move with respect to the syringe 2. As a consequence, both the plunger rod 20 and the syringe 2 are driven in the distal direction, thereby realizing the insertion of the needle 3 into the injection site 5 (see FIG. 8B). During this step, the first helical spring 8 therefore acts as biasing means for moving the syringe 2 from its first position to its second position, said second position being an insertion position (needle inserted into the injection site).

During this distal movement of the syringe 2, the needle protection cover 30 has remained in abutment against the patient's skin. As a result, the syringe has moved distally with respect to the needle protection sleeve 30 and has caused the second helical spring 9 to reach a more compressed state than in the before use position, as shown on FIG. 8B.

In this position of the device 1 where the needle 3 is inserted in the injection site 5, the needle protection sleeve 30 is blocked in distal translation by the patient's skin. Consequently, from this step on, the removal of the device 1 from the skin of the patient will automatically cause the expansion of the second helical spring 9 and therefore the movement of the needle protection sleeve 30 to its final position, in which it surrounds the needle 3 (see FIG. 9A-B). The device 1 of the invention is therefore very safe and requires no additional effort from the user for activating the protection of the needle 3 as soon as the insertion step is completed, regardless from the fact that the injection step has started or not.

Once the needle 3 is inserted in the injection site 5, the first helical spring 8 continues to expand towards a third state, less stressed than its second state, as shown on FIG. 8B. The syringe 2 being now blocked in translation against the patient's skin, the distal force of the first helical spring 8 reaches a value sufficient for overcoming both the friction force between the shaft 21 of the plunger rod 20 and the syringe 2 provided by the rubber part 114 and the gliding force of the stopper 6. The expansion of the first helical spring 8 therefore causes the distal movement of the stopper 6 within the syringe 2, via the plunger rod 20 and the linking member 60 which continues its distal movement, still guided by the two longitudinal ridges 46 of the holder 40. The injection therefore takes place and the product 7 is expelled into the injection site 5 through the needle 3 until the stopper 6 reaches the distal end of the syringe 2 (see FIG. 8B).

During this step, the first helical spring 8 acts as urging means for distally moving the stopper 6 once the syringe 2 has reached its second position, and therefore realize injection of the product 7. As such, in the example shown on these figures, the biasing means and the urging means are under the form of a single helical spring, going from a first state to a second state, and then from said second state to a third state, said third state being less stressed than said second state, said second state being less stressed than said first state.

Whatever the necessary intrinsic force of the first helical spring 8 for completing both the insertion step and the injection step, the effort required from the user at the beginning of the process for initiating the insertion step remains low thanks to the particular arrangement of the deactivating member 80 and the retaining piece 70 in the device.

In embodiments not shown, the biasing means and the urging means could be under the form of two different helical springs.

The user then removes the device 1 from the injection site 5, and, as already explained above, the second helical spring 9 naturally expands from its compressed state to a rest state and causes the needle protection sleeve 30 to move distally with respect to the syringe 2 and to cover the needle 3, as shown on FIGS. 9A-B. The needle protection sleeve 30 therefore acts as needle protection means movable with respect to the syringe 2 when the syringe 2 is in its second position with respect to said housing 10 between an insertion position, in which the distal tip of the needle 3 extends beyond the distal end of the needle protection means, and a final position, in which the distal tip of the needle does not extend beyond the distal end of the needle protection means and is surrounded by the needle protection means. During this step, the second helical spring 9 acts as elastic return means for automatically moving said needle protection means (needle protection sleeve 30) from its insertion position to its final position, upon removal of the device 1 from the injection site 5 by the user.

The device 1 of the invention has therefore advantages for the pharmaceutical companies, which may fill the syringe 2 on a first site, and assemble the syringe 2 in the housing 10 on this first site, while the motor part 100 of the device 1 may be assembled on a second site. The motor part 100 and the housing part 200 may then be connected to each other so as to obtain the device 1. Furthermore, the motor part 100 may be adapted to different sizes and/or volumes of syringes.

The device of the invention allows having biasing means, such as the first helical spring 8 having a high intrinsic force for completing the injection of products requiring such a high distal force, such as viscous drugs, while at the same time requiring only a low force from the user at the time of triggering the injection, in particular a transversal force.

The invention claimed is:

1. A device for injection of a product into an injection site, said device comprising:
    a housing having a longitudinal axis A and receiving a container for the product to be injected, said container being aligned on said longitudinal axis A, said container being substantially closed at a proximal end by a stopper, said stopper being capable of being moved distally within said container so as to expel the product to be injected, and at a distal end by a needle for the exit of the product to be injected, said container being movable with respect to said housing between a first position, in which the needle does not extend beyond a distal end of the housing, and a second position, distally spaced with respect to said first position, in which the needle extends beyond the distal end of the housing,
    a biasing element coupled to said housing and structured to produce a distal force along a longitudinal axis B when transitioning from a first state to a second state, said second state being less stressed than said first state, said longitudinal axis B being laterally spaced with respect to said longitudinal axis A along a transversal direction R,
    a linking element for coupling said biasing element to said container at least from said first position to said second position of the container, said linking element being shaped and dimensioned so as to transmit said distal force to said container when said biasing element transitions from said first state to said second state so as to move said container from its first position to its second position,
    a retainer element coupled to said container and to said housing in the first position of the container, for releasably maintaining said biasing element in said first state, said retainer element being capable of moving from a passive condition, in which it maintains said biasing element in said first state, to an active condition, in which said biasing element is free to transition to said second state,
    wherein the device further comprises
    a deactivating element coupled to said retaining element, capable of moving with respect to the retainer element from a first position, in which said retainer element is in a passive condition, to a second position, offset from said first position along said transversal direction R, in which said retainer element is in said active condition, and
    a trigger element for moving said deactivating element from said first position to said second position, wherein said trigger element is configured to be actuated in said transversal direction R,
    wherein said retainer element comprises at least one deflectable leg capable of deflecting radially with respect to longitudinal axis B between a locked position, in which the retainer element is in said passive condition, and a free position in which the retainer element is in said active condition, said deactivating element comprises at least one cooperating surface, said cooperating surface causing said legs to move from a locked position to a free position when said deactivating element is moved from said first position to said second position along transversal direction R.

2. The device of claim 1, wherein the linking element comprises at least a linking member aligned on said transversal direction R, said linking member connecting said biasing element to said container.

3. The device of claim 2, wherein said biasing element is a helical spring and said device further comprises a plunger rod for distally pushing said stopper within said container during an injection step, said linking member is connected to said container via said plunger rod, said linking member further comprising a tubular lodging receiving said helical spring, said helical spring being in distal abutment on a distal transversal wall of said tubular lodging and being in proximal abutment on a proximal transversal wall fixed with respect to said housing.

4. The device of claim 1, wherein said triggering element comprises a button mounted in pivoting relationship with respect to said housing, said button comprising a pushing surface accessible to a user for pivoting said button, said button further comprising an actuating surface capable of cooperating with a surface of said deactivating element, for moving said deactivating element from said first position to said second position, when the button is caused to pivot.

5. The device of claim 1, further comprising : a locking element for preventing said triggering element from moving said deactivating element from said first position to said second position, said locking element being releasable, and a releasing element for releasing the locking element.

6. The device of claim 1, further comprising an urging element coupled to said stopper and to said housing when said container is in said second position, said urging element being designed for distally moving said stopper when transitioning from a first state to a second state, said second state being less stressed than said first state, thereby realizing injection of the product.

7. The device of claim 3, wherein said helical spring is capable of transitioning from said second state to a third state, during which said helical spring moves the stopper distally, said third state being less stressed than said second state, said helical spring forms both said biasing and an urging element.

8. The device of claim 1, further comprising: a needle protection element, at least partially received within said housing, and movable with respect to said container when said container is in said second position with respect to said housing, between an insertion position, in which a distal tip of the needle extends beyond the distal end of the needle protection element, and a final position, in which the distal tip of the needle does not extend beyond the distal end of the needle protection element, and an elastic return, coupled to said needle protection element and to said container, and designed for automatically moving said needle protection element from said insertion position to said final position, upon removal of the device from an injection site by a user.

9. The device of claim 1, wherein said device is driven by a motor part and a housing part, said motor part comprising at least the biasing element, the linking element, the retaining element, the deactivating element, and the triggering element and said housing part comprising at least said housing receiving the container, and optionally the needle protection element and the elastic return, said device further comprising a connecting element for connecting said motor part to said housing part at time of use.

* * * * *